United States Patent [19]

Gruber

[11] 4,104,064
[45] Aug. 1, 1978

[54] PHOTOELECTROPHORETIC IMAGING METHOD EMPLOYING DINAPHTHO-FURAN-DIONE PIGMENTS

[75] Inventor: Robert J. Gruber, Pittsford, N.Y.

[73] Assignee: Xerox Corporation, Stamford, Conn.

[21] Appl. No.: 732,580

[22] Filed: Oct. 15, 1976

Related U.S. Application Data

[62] Division of Ser. No. 630,479, Nov. 5, 1975, Pat. No. 4,017,311, which is a division of Ser. No. 492,555, Jul. 29, 1974, Pat. No. 3,957,829.

[51] Int. Cl.² .............................................. G03G 17/04
[52] U.S. Cl. ...................................... 96/1 PE; 96/1.2; 96/1.3; 204/181 E
[58] Field of Search ................................ 96/1 PE, 1.2; 204/181 PE

[56] References Cited

U.S. PATENT DOCUMENTS

| | | | |
|---|---|---|---|
| 2,870,168 | 1/1959 | Randall et al. | 260/346.2 M |
| 2,940,983 | 6/1960 | Sartori | 260/346.2 M |
| 2,967,870 | 1/1961 | Randall et al. | 260/346.2 R |
| 3,033,879 | 5/1962 | Sartori | 260/346.2 M |
| 3,147,283 | 9/1964 | Frey | 260/346.2 M |
| 3,384,488 | 5/1968 | Fulagin et al. | 96/1.5 X |
| 3,384,566 | 5/1968 | Clark | 96/1 PE X |
| 3,560,360 | 2/1971 | Carreira et al. | 96/1 PE X |
| 3,811,883 | 5/1974 | Zographos et al. | 96/1.5 |

FOREIGN PATENT DOCUMENTS

461,650 2/1925 Fed. Rep. of Germany.

OTHER PUBLICATIONS

Suryanarayana et al., "Proceedings of the Indian Academy of Science," 1953, pp. 81 and 88.

Primary Examiner—David Klein
Assistant Examiner—John R. Miller

[57] ABSTRACT

There are described novel yellow compounds which are represented by the formula

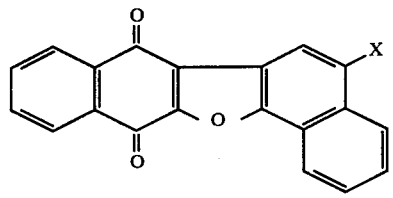

wherein X is a member selected from the group consisting of

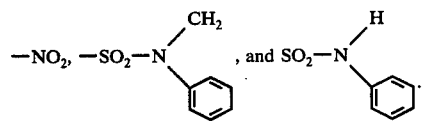

The compounds may be used for various applications and preferably are utilized as imaging particles in the photoelectrophoretic imaging method.

6 Claims, 1 Drawing Figure

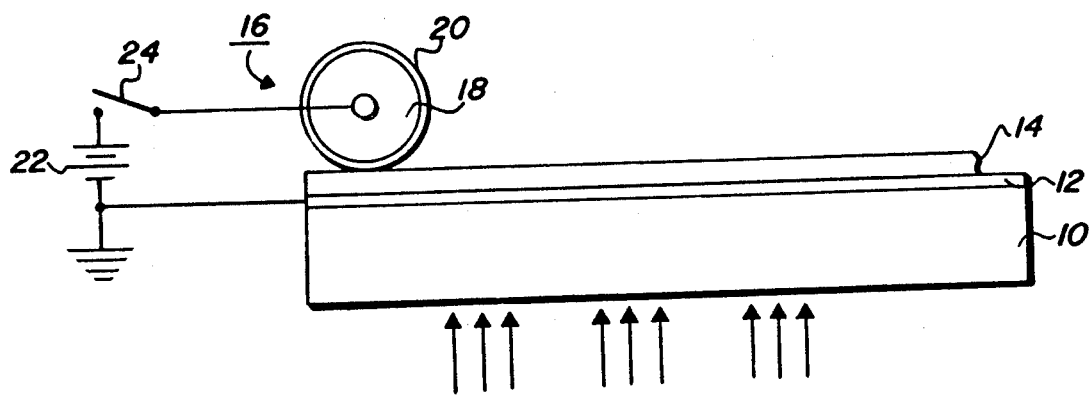

PHOTOELECTROPHORETIC IMAGING METHOD EMPLOYING DINAPHTHO-FURAN-DIONE PIGMENTS

BACKGROUND OF THE INVENTION

This is a divisional of application Ser. No. 630,479 filed Nov. 10, 1975 (U.S. Pat. No. 4,017,311) which is, in turn, a divisional of Ser. No. 492,555 filed July 29, 1974 (U.S. Pat. No. 3,957,829).

The present invention relates to novel compounds and more particularly to novel yellow pigments which are useful in the photoelectrophoretic imaging method.

Photoelectrophoretic imaging methods which are capable of producing monochromatic or polychromatic images are described and claimed in various U.S. Pat. Nos. including, for example, 3,384,565; 3,384,566; and 3,385,488. In photoelectrophoretic imaging there is provided an imaging suspension which comprises imaging particles suspended in a carrier liquid. Typically, a layer of the imaging suspension is arranged between a pair of electrodes, subjected to an applied electrical field and exposed to an imagewise pattern of activating electromagnetic radiation. At the completion of these method steps, there are typically formed complementary images at the surfaces of the electrodes. An essential component of the photoelectrophoretic imaging system is the imaging particles which must be electrically photosensitive and which apparently undergo a net change in charge polarity upon exposure to activating electromagnetic radiation through interaction with one of the electrodes. The imaging particles used in this imaging system should have intense pure colors and be highly photosensitive.

The prior art teaches various types of pigments which are suitable for use in photoelectrophoretic imaging. Further, other prior art disclosures which are unrelated to photoelectrophoretic imaging teach compounds which may be found to be useful in this imaging system. For example, the preparation of 2-bromo-3,4-benzobrazanquinone as described in "Proceedings of the Indian Academy of Science", B. Suryanarayana and B. Tilak, page 81, 1953, and 2-chloro-3,4-benzobrazanquinone is described in German Pat. No. 461,650. These compounds are yellow pigments. Nevertheless, there continue to be discovered new pigments which may be used in the photoelectrophoretic imaging mode. The present invention relates to novel yellow pigments which may be used in such an imaging system.

SUMMARY OF THE INVENTION

It is therefore an object of this invention to provide novel compositions of matter.

It is another object to provide novel yellow pigments.

It is a further object of the invention to provide electrically photosensitive yellow pigments having advantageous optical absorption characteristics.

Yet another object is to provide photoelectrophoretic imaging suspensions.

Still another object is to provide photoelectrophoretic imaging methods employing the novel electrically photosensitive yellow pigments.

BRIEF SUMMARY OF THE INVENTION

These and other objects and advantages are accomplished in accordance with the present invention by providing yellow compounds which are represented by the general formula

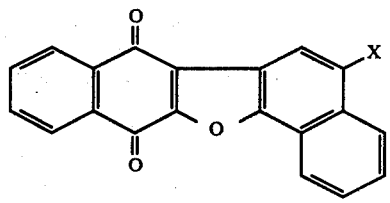

wherein X is a member selected from the group consisting of

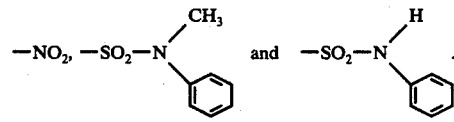

The compounds of the invention are suitable for use in various applications including xerographic imaging and photoelectrophoretic imaging.

BRIEF DESCRIPTION OF THE DRAWINGS

For a better understanding of the invention as well as other objects and further features thereof, reference is made to the following detailed description of various preferred embodiments thereof taken in conjunction with the accompanying drawing wherein the FIGURE is a partially schematic cross-sectional view of an embodiment of a photoelectrophoretic imaging system.

DESCRIPTION OF THE PREFERRED EMBODIMENTS

The novel compounds of the invention as illustrated by formula I are prepared according to the following reaction.

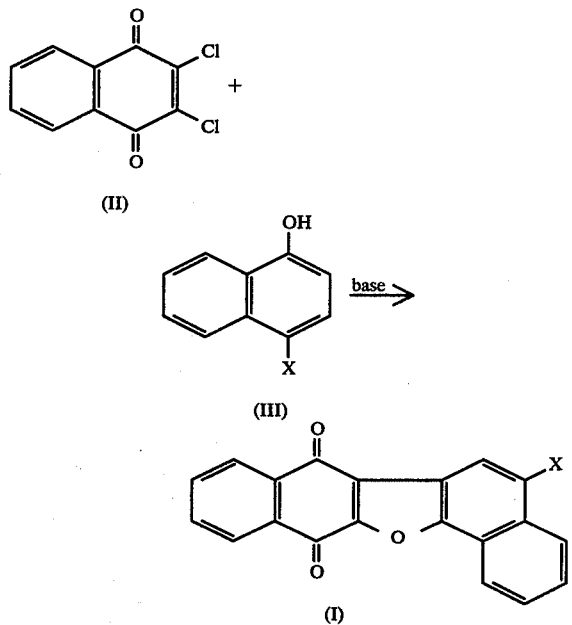

where X is as defined above. The reaction is generally carried out in solution and in the presence of an acid acceptor by refluxing for from about 1 to about 3 hours. The solvent may be any suitable material such as, for example, pyridine, dimethylformamide, xylene, isopropanol, and mixtures thereof. The acid acceptor may be any suitable base such as, for example, pyridine, sodium carbonate, sodium bicarbonate, and triethylamine. In one embodiment, pyridine may be advantageously employed as both the solvent and the acid acceptor.

As noted above, the novel compounds provided according to the present invention may be used in various applications. For example, these compounds may be used as electroscopic marking material in the well known xerographic reproduction process. Preferably the compounds are utilized as imaging particles in a photoelectrophoretic imaging method. Generally, the compounds may be used in any application where intensely yellow colored materials are desirable.

Generally, as aforesaid, in photoelectrophoretic imaging a layer of an imaging suspension is arranged between a pair of electrodes subjected to an electrical field and exposed to an imagewise pattern of activating electromagnetic radiation. Preferably, the electrical field applied across the imaging suspension layer is established between electrodes having certain preferred properties, i.e., an injecting electrode and a blocking electrode and the exposure to activating radiation occurs simultaneously or substantially simultaneously with field application. However, as is taught in various prior art patents including, for example, U.S. Pat. Nos. 3,595,770; 3,647,659; and 3,447,934 such a wide variety of materials and modes for associating an electrical bias therewith, e.g., charged insulating webs, may serve as the electrodes, that is, the means for applying the electrical field across the imaging suspension layer, that opposed electrodes generally can be used; and the exposure and field application steps may be sequential. In preferred embodiments of the practice of the photoelectrophoretic imaging method as described herein, one electrode may be referred to as the injecting electrode and the opposite electrode as the blocking electrode. The terms "blocking electrode" and "injecting electrode" as used throughout this application should be understood and interpreted in the context of these comments.

Referring now to the figure, there is illustrated in partially schematic cross-sectional form, an embodiment of a photoelectrophoretic imaging system wherein a substantially transparent substrate 10 and a substantially transparent conductive coating 12 comprise a substantially transparent electrode. A typical suitable transparent electrode material is commercially available under the name NESA glass from Pittsburgh Plate Glass Co., and comprises a thin optically transparent layer of tin oxide deposited on a transparent glass substrate. This electrode will be referred to hereinafter as the "injecting electrode". Coated on the surface of the injecting electrode is a layer of an imaging suspension 14 comprising finely divided electrically photosensitive pigment particle of the present invention dispersed in a carrier liquid. The term "electrically photosensitive" is applied to the imaging particles dispersed in the carrier liquid is intended to encompass any particle which, once attracted to the injecting electrode, will migrate away from it under the influence of an electrical field when the particle is exposed to electromagnetic radiation. For a detailed theoretical description of the apparent mechanism of operation of photoelectrophoretic imaging see U.S. Pat. Nos. 3,384,565 and 3,384,566.

While the novel electrically photosensitive pigments disclosed herein may be utilized along without the presence of other colored pigment particles, any other suitable electrically photosensitive pigment may be incorporated in the suspension. It should be noted that any suitable electrically photosensitive pigment particles may be used including, for example, the types disclosed in U.S. Pat. Nos. 2,980,847 and 3,681,064 as well as those described in other prior art patents. Any suitable insulating liquid may be used as the carrier liquid in the imaging suspension. Typical insulating carrier liquids include: long chain saturated aliphatic hydrocarbons such as decane, dodecane, and tetradecane; kerosene fractions such as Sohio Odorless solvents available from the Standard Oil Company of Ohio, Isopar G commercially available from the Humble Oil Company of New Jersey; molten thermoplastic materials such as paraffin wax and bees wax; mineral oil; vegetable oils such as linseed oil and olive oil; marine oils such as sperm oil and codliver oil; silicone oils such as dimethypolysiloxane (Dow Corning Company); fluorinated hydrocarbons such as Freon; and mixtures thereof. The imaging suspension may also contain a sensitizer and/or binder.

Above the imaging suspension layer 14 is arranged a second electrode, generally designated 16, commonly referred to as the blocking electrode, which in this embodiment is shown as a roller but which may be of any suitable configuration such as for example, a flat plate. The blocking electrode comprises a conductive central core 18 covered with a layer of a suitable electrically insulating material 20 such as, for example, paper, coated paper such as baryta paper, polymeric materials such as Tedlar, Mylar (available from duPont) and the like. It is preferred to employ blocking material layer 20 to eliminate the possibility of electrical shorting occurring across the electrodes. Although the injecting electrode has been illustrated as transparent and exposure as being effected through the injecting electrode, it should be noted that the blocking electrode could be the transparent electrode and exposure could be made through it where it is so desired. It should also be noted that the electrode through which exposure is made need not be completely transparent to the activating radiation but rather it may only be partially transparent; the only requirement is that the electrode transmit enough activating electromagnetic radiation to cause imaging to occur. It should also be understood that although there has been illustrated a particular electrode configuration the photoelectrophoretic imaging method of the invention may be practiced with either or both of the electrodes in the form of drums, rollers, flat plates, traveling webs, etc.

The blocking electrode 16 is connected to one side of potential source 22 through a switch 24. The opposite side of potential source 23 is connected to the conductive layer 14 of the injecting electrode so that when switch 24 is closed an electrical field is applied across the imaging suspension layer 14 between the electrodes. The imaging suspension is exposed to an imagewise pattern of activating electromagnetic radiation (represented by the arrows) through the transparent injecting electrode. The imagewise electromagnetic radiation may be provided by any suitable means. In operation, blocking electrode 16 is caused to roll across the surface of the injecting electrode with switch 24 closed during the period of exposure. Upon completion of the roller traverse across the injecting electrode there are formed complementary images on the surfaces of the electrodes. The images may be fixed to the surfaces of the electrodes by any suitable technique such as by solvent evaporation, spray coating and the like, or preferably the images may be transferred to a receiver material and fixed thereto in which case the electrodes may be cleaned and reused in a recyclible imaging system. The image transfer step may be effected by adhesive pickoff techniques or preferably by electrostatic field transfer while the image is still set. Any suitable material may be used as the receiver material for the images including, for example, paper and various transparent polymeric materials such as Myler, Tedlar, and the like.

When used in the course of the present discussion, the term "injecting electrode" should be understood to mean an electrode which will preferably be capable of exchanging charge with the photosensitive particles of the imaging suspension when the suspension is exposed to light so as to allow for a net change in the polarity of the activated particles. By the term "blocking electrode" is meant one which is substantially incapable of injecting charge carriers into the above-mentioned photosensitive particles as compared to the injecting electrode, thus substantially blocking direct current. The use of the blocking electrode serves to minimize particle oscillation in the system and to prevent electrical shorting between the electrodes.

It is preferred that the injecting electrode be an optically transparent material, such as glass overcoated with a conductive material such as tin oxide, copper, copper iodide gold or the like; however, other suitable materials including many semiconductive materials such as raw cellophane, which are ordinarily not thought of as being conductors but which are still capable of accepting injected charge carriers of the proper polarity under the influence of an applied electric field may be used within the course of the present invention.

The blocking layer of the imaging electrode, on the other hand, is selected so as to prevent or greatly retard the injection of charge carriers into the photosensitive pigment particles when the particles reach the surface of this electrode. Although a blocking electrode material need not necessarily be used in the system, the use of such a layer is preferred because of the markedly improved results which it is capable of producing. It is preferred that the blocking layer, when used, be either an insulator or a semiconductor which will not allow for the passage of sufficient charge carriers, under the influence of the applied field, to discharge the particles bound to its surface, thereby preventing particle oscillation in the system. The result is enhanced image density and resolution. Even if the blocking layer does allow for the passage of some charge carriers to the photosensitive particles, it still will be considered to fall within the class of preferred materials if it does not allow for the passage of sufficient charge so as to recharge all the particles to the opposite polarity.

Exemplary of the preferred blocking materials used are baryta paper, Tedlar, Mylar, and polyurethane. Any other suitable materials having a resistivity of at least about $10^7$ ohms-cm may be employed. Typical materials in this resistivity range include cellulose acetate coated papers, cellophane, polystyrene and polytetrafluoroethylene. The core of the blocking electrode generally will consist of a material which is fairly high in electrical conductivity. Typical conductive materials including conductive rubber, and metal foils of steel, aluminum. copper and brass have been found suitable. Preferably, the core of the electrode will have a high electrical conductivity in order to establish the required field differential in the system; however, if a material having a low conductivity is used, a separate electrical connection may be made to the back of the blocking layer of the blocking electrode. For example, the blocking layer or sleeve may be a semiconductive polyurethane material having a resistivity of from about $10^8$ to $10^9$ ohms-cm. If a hard rubber non-conductive core is used when a metal foil may be employed as a backing for the blocking sleeve. Other materials that may be used in conjunction with the injecting and blocking electrodes and other photosensitive particles which may be used as the electrically photosensitive pigments and the various conditions under which the process operates may be found in the U.S. patents described above.

For monochromatic imaging, particles of a single color are dispersed in the carrier liquid and exposed to an image. A single color image results, corresponding to conventional black-and-white photography. Any desired single color image can be obtained in this fashion.

For polychromatic imaging, one or more other suitable pigment particles may be employed in combination with the pigments of the present invention. The selection depends largely upon the photosensitivity and the spectral sensitivity desired. The particles are selected so that those of different colors respond to different wavelengths in the visible spectrum corresponding to their principal absorption bands. Also, the pigments should be selected so that their spectral response curves do not have substantial overlap, thus allowing for good color separation and subtractive multicolor image formation.

In a typical polychromatic system, the particle dispersion may include cyan colored particles which are sensitive mainly to red light, magenta colored particles which are sensitive mainly to green light, and yellow colored particles which are sensitive mainly to blue light. When mixed together in a carrier liquid, these particles produce a black-appearing liquid. When one or more of the particles are caused to migrate from injecting electrode 1 toward the second electrode, they leave behind particles which produce a color equivalent to the color of the activating light. Thus, for example, red light exposure causes the cyan colored pigment to migrate leaving behind the magenta and yellow pigments which combine to produce red in the final image. In the same manner, blue and green colors are reproduced by removal of yellow and magenta, respectively. When white light impinges upon the mix, all pigments migrate, leaving no pigmentary color on the electrodes. No exposure leaves behind all pigments which combine to produce a black image. This is an ideal technique of subtractive color imaging in that the pigment particles are each composed of a single component which is both the image colorant and the photosensitive medium.

It has been found that the photosensitive compounds of the present invention are very effective when used in a single-color photoelectrophoretic imaging system. Their good spectral response and high photosensitivity result in dense, brilliant images. These compounds are also useful in polychromatic imaging systems.

From about 2 to about 10 percent pigment by weight have been found to produce good results. The addition of small amounts (generally ranging from 0.5 to 5 mol. percent) of electron donors or acceptors to the suspensions may impart significant increases in system photosensitivity.

A wide range of voltages may be applied between the electrodes in the system. For good image resolution, high image density and low background it is preferred that the potential applied be such as to create an electric field of at least about 300 volts per mil across the imaging suspension. For example, when the imaging suspension is coated to a thickness of about 1 mil, the electrode spacing will be such that an applied potential of about 300 volts produces a field across the suspension of about 300 volts per mil. Potentials as high as 8,000 volts may be applied to produce images of high quality. As is apparent, the applied potential necessary to obtain the desired field strength will vary depending upon the interelectrode gap as well as the type and thickness of the blocking material utilized. The imaging suspension may be coated to a thickness of up to about 25 microns.

The invention will now be further described in detail with respect to specific preferred embodiments thereof by way of Examples, it being understood that these are intended to be illustrative only and the invention is not limited to the materials, percentages, conditions, etc. recited therein. All parts and percentages are by weight unless otherwise specified.

The pigments are tested in an apparatus wherein one of the electrodes is in roller configuration and the other is a flat plate NESA glass electrode with the imaging suspension layer being coated on the latter. Exposure is made through the NESA glass electrode. The roller electrode is a blocking electrode and comprises an approximately 2½ inch diameter metal core surrounded by an approximately ¼ inch layer of relatively soft polyurethane which in turn is surrounded by an approximately 2 mil thick layer of aluminized Tedlar with the conductive surface of the Tedlar being arranged adjacent the polyurethane layer. The conductive surface of the NESA glass electrode is connected in series with a switch, a potential source and the conductive surface of the Tedlar film which makes up the surface of the blocking electrode. During imaging the blocking electrode is moved across the NESA glass electrode surface at a speed of about 3 inches per second. The NESA glass electrode is about 4 inches square and is exposed with a light intensity of about 1000 foot-candles.

Unless otherwise indicated, about seven percent by weight of the indicated pigment in each example is suspended in Sohio Odorless Solvent 3440 and the magnitude of the applied voltage is about 2500 volts with respect to the NESA electrode. In operation the electrodes are in virtual contact, spaced by the particle suspension layer thus providing an electrode spacing of from about 5 to about 25 microns (0.2 to 1 mil). Exposure is made with a tungsten lamp through a series of Wratten filters (red 29, green 61, and blue 47B) and white light.

EXAMPLE I

Preparation of 5-nitrodinaphtho-[1,2-b; 2'3'-]-furan-7,12-dione

A solution of 53.2 g (0.526 mole.) of triethylamine in 100 ml of isopropanol is added to a refluxing mixture of 50.0 g (0.264 mole.) of 4-nitro-1-naphthol and 62 g (0.071 mole.) of 2,3-dichloro-1,4-naphthoquinone in 1 liter of isopropanol over a period of 1 hour. The temperature is then maintained at reflux for an additional 3½ hours. The resulting yellowish-brown mixture is filtered and washed with methanol until the filtrate is light yellow. The solid is then slurried in several 500 ml portions of hot de-ionized water and again washed with methanol to yield 55 grams of a yellowish solid, m.p. 274°–275° C. The overall yield is 25%. The ir (KBr) shows strong bands at 5.95 (C=O), 6.50 ($NO_2$), 7.45 ($NO_2$), 8.05, 10.50, 12.90 and 14.5$\mu$; mass spectrum (50 eV) m/e 343, 313, 297, 285, 257, 241, 229, 213, and 106.5. $C_{20}H_9NO_5$ requires 69.97% C; 2.65% H; 4.09% N and 23.29% O. Elemental analysis of the compound prepared found 69.64% C; 2.50% H; 4.02% N and 23.84% O.

A greenish-yellow polymorph can be obtained by crystallizing from dimethylformamide or quenching a solution of the pigment in quinoline, pyridine, or dimethylformamide with ethanol.

When utilized in the photoelectrophoretic imaging method the compounds exhibit good electrical photosensitivity.

EXAMPLE II

Preparation of 5-(N-methyl-N-phenyl-sulfonamido)-dinaphtho-[1,2-b; 2',3'-d]-furan-7,12-dione A. Preparation of 1-hydroxy-4-(N-methyl-N-phenyl-sulfonamido)-naphthalene.

To 300 ml of acetic anhydride and 150 ml of chlorobenzene is added 26 grams (0.1 mole.) of 1-hydroxynaphthalene-sulfonic acid sodium salt and the mixture is heated to reflux for about 4 hours. The mixture is then cooled to 25° C, filtered and the solid is slurried in petroleum ether and filtered again. The resulting solid is slurried in 400 ml of benzene and 10 ml of dimethylformamide to which is added at 25° C, 20 ml of thionyl chloride. After the mixture is heated to about 80° C for about 15 minutes it is held at 55° C for about 1 hour. The excess thionyl chloride and 300 ml of solvent are removed under vacuum at 65° C. To the resulting mixture are added 300 ml chlorobenzene and 20 grams of aniline between 5°–8° C. This mixture is then washed with water and the organic phase is dried over $M_gSO_4$ and stripped under vacuum to provide about 25 grams of an oil. This oil is dissolved in 180 ml of methanol to which is added 6.6 grams of 85% potassium hydroxide at room temperature. This mixture is then stirred for about 2 hours, quenched into 500 ml of de-ionized water, filtered to clarify, the aqueous layer extracted with benzene to remove non-acidic material and finally acidified with concentrated hydrochloric acid. The resulting solid is filtered, washed with water and there is obtained about 13 grams of a white solid having a melting point of 198°–200° C. The overall yield is 46%. The ir (KBr) shows strong bands at 3.08 (OH), 6.35, 8.70 ($SO_2$), 8.90, 10.40, 12.00, 12.78, 14.38 and 14.80$\mu$. The nmr spectrum (DMSO $d_6$) shows a peak at 7.00(s), 7.43 multiplet centered at 8.25, 11.15(s) and 11.88(s), $C_{16}H_{13}NO_3S$ requires 64.20% C; 4.38% H; 4.68% N; 10.71% S and 16.03% O. Elemental analysis of this compound found 64.08% C; 4.49% H; 4.76% N; 10.46% S and 16.21% O.

B. Preparation of Pigment

A solution of 10 g (0.1 mole.) of triethylamine in 50 ml of isopropanol is added to a mixture of 13 g (0.042 mole.) of 1-hydroxy-4-(N-methyl-N-phenyl-sulfonamido)-naphthalene, 11 g (0.05 mole.) of 2,3-dichloro-1,4-naphthoquinone in 150 ml of isopropanol over a 20 minute period at reflux. The mixture is then refluxed an additional hour, and the resultant yellowish mixture is filtered hot, washed with acetone and then with hot de-ionized water to give 7.5 g of a yellowish solid, m.p. 229°–230° C. This solid is then sequentially crystallized from 54 ml of pyridine and then quinoline to give 4.7 g of a bright greenish-yellow pigment, m.p.

230°–230.5° C. $C_{27}H_{17}NO_5S$ requires 69.37% C, 3.67% H; 3.00% N; 6.86% S and 17.10% C. Elemental analysis found 69.24% C; 3.51% H; 3.00% N, 6.68% S and 17.57% O.

When utilized in the photoelectrophoretic imaging method the compound exhibits good electrical photosensitivity.

EXAMPLE III

Preparation of 5-(N-phenylsulfonamido)-dinaphtho-[1,2-b; 2′,3′-d]-furan-7,12-dione A solution of 7.1 g (0.7 mole.) of triethylamine in 25 ml is isopropanol is added to a refluxing mixture of 10 g (0.33 mole.) of 1-hydroxy-4(N-phenylsulfonamido)-naphthalene (m.p. 132°–133° C) and 8 g (0.35 mole.) of 2,3-dichloro-1,4-naphtho-quinone in 150 ml of isopropanol over a 30 minute period. The mixture is refluxed for 2 hours, filtered, and washed first with methanol and then with hot de-ionized water to give 5.5 g of a yellowish solid, m.p. 331°–333° C. This solid is dissolved in 800 ml of dioxane (80° C), filtered to clarify, and then admixed with 1200 ml of de-ionized water to give 5.0 g of a yellow powder, m.p. 324° C. This is further purified by dissolving it in 100 ml of quinoline at 129° C, adding the hot solution to 125 ml of methanol, cooling to 10° C and filtering to give 4.3 g, m.p. 333°–334° C. The pigment is finally crystallized from quinoline yielding a bright greenish-yellow solid. $C_{26}H_{15}NO_5S$ requires 68.86% C; 3.33% H; 3.09% N; 7.07% S and 17.65% O. Elemental analysis found 68.55% C; 2.21% H; 3.25% N; 7.07% S and 17.92% O.

When utilized in the photoelectrophoretic imaging method the compound exhibits good electrical photosensitivity.

Although the invention has been described with respect to various preferred embodiments thereof it is not intended to be limited thereto but rather those skilled in the art will recognize that variations and modifications may be made therein which are within the spirit of the invention and the scope of the claims.

What is claimed is:

1. A photoelectrophoretic imaging method comprising the steps of (a) applying a layer of an imaging suspension comprising an electrically photosensitive pigment particle represented by the general formula

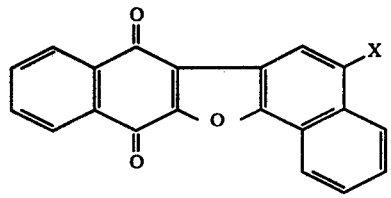

wherein X is defined as a member selected from the group consisting of

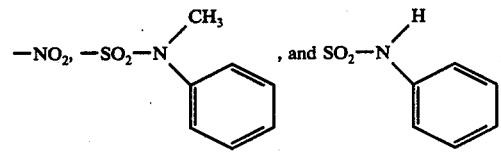

in an electrically insulating carrier liquid, between a pair of electrodes, at least one of which is transparent;

(b) subjecting said suspension layer to an electrical field; and substantially simultaneously therewith (c) exposing said suspension layer to an imagewise pattern of activating electromagnetic radiation to which at least a portion of said pigment particles are sensitive, through said transparent electrode; whereby an image is formed on at least one of the said electrodes.

2. The method as defined in claim 1 and further including the step of fixing said image to said electrode.

3. The method as defined in claim 1 and further including the step of transferring said image to a receiver member.

4. The method as defined in claim 3 and further including the step of fixing said image to said receiver member.

5. The method as defined in claim 1 wherein said imaging suspension includes cyan pigment particles, magenta pigment particles and yellow pigment particles.

6. The method as defined in claim 1 wherein one of said electrodes is a blocking electrode.

* * * * *